(12) United States Patent
Modarres

(10) Patent No.: US 8,473,043 B1
(45) Date of Patent: Jun. 25, 2013

(54) NEURO-BEHAVIORAL TEST METHOD FOR SCREENING AND EVALUATING THERAPY FOR ADHD AND SYSTEM

(75) Inventor: Mo Modarres, Cleveland Heights, OH (US)

(73) Assignee: Neuro Wave Systems Inc., Cleveland Heights, OH (US)

( * ) Notice: Subject to any disclaimer, the term of this patent is extended or adjusted under 35 U.S.C. 154(b) by 2140 days.

(21) Appl. No.: 11/454,485

(22) Filed: Jun. 16, 2006

Related U.S. Application Data

(63) Continuation-in-part of application No. 11/021,594, filed on Dec. 22, 2004, now Pat. No. 7,865,234.

(60) Provisional application No. 60/691,749, filed on Jun. 17, 2005.

(51) Int. Cl.
*A61B 5/04* (2006.01)

(52) U.S. Cl.
USPC .......................................................... 600/544

(58) Field of Classification Search
USPC ................................................. 600/544, 545
See application file for complete search history.

(56) References Cited

U.S. PATENT DOCUMENTS

| | | | |
|---|---|---|---|
| 5,287,859 A * | 2/1994 | John ............................. | 600/544 |
| 5,520,176 A * | 5/1996 | Cohen ........................... | 600/300 |
| 5,813,993 A * | 9/1998 | Kaplan et al. ................. | 600/544 |
| 5,913,310 A * | 6/1999 | Brown ........................... | 128/897 |
| 5,918,603 A * | 7/1999 | Brown ........................... | 128/897 |
| 5,940,801 A * | 8/1999 | Brown ............................. | 705/2 |
| 6,032,065 A * | 2/2000 | Brown ........................... | 600/383 |
| 6,052,619 A * | 4/2000 | John ............................. | 600/544 |
| 6,053,739 A * | 4/2000 | Stewart et al. ................ | 434/236 |
| 6,097,980 A * | 8/2000 | Monastra et al. ............. | 600/544 |
| 6,115,631 A * | 9/2000 | Heyrend et al. ............... | 600/544 |
| 6,195,576 B1 * | 2/2001 | John ............................. | 600/409 |
| 6,241,686 B1 * | 6/2001 | Balkin et al. .................. | 600/544 |
| 6,385,486 B1 * | 5/2002 | John et al. ..................... | 600/544 |
| 6,419,629 B1 * | 7/2002 | Balkin et al. .................. | 600/300 |
| 6,496,724 B1 * | 12/2002 | Levendowski et al. ....... | 600/544 |
| 6,527,715 B2 * | 3/2003 | Balkin et al. .................. | 600/300 |
| 6,530,884 B2 * | 3/2003 | Balkin et al. .................. | 600/300 |
| 6,553,252 B2 * | 4/2003 | Balkin et al. .................. | 600/544 |
| 6,622,036 B1 * | 9/2003 | Suffin ........................... | 600/544 |
| 6,625,485 B2 * | 9/2003 | Levendowski et al. ....... | 600/544 |

(Continued)

OTHER PUBLICATIONS

Kovatchev, B. A psychophysiological marker of attention deficit disorder—defining the EEG consistency index. Applied Psychophysiology and Biofeedback 26(2): 127-40, 2001.

(Continued)

*Primary Examiner* — Navin Natnithithadha

(74) *Attorney, Agent, or Firm* — Brian M. Kolkowski; Robert K. Schmidt

(57) ABSTRACT

A new neuro-behavioral test with analysis algorithms has been developed for use in screening individuals for attention deficit hyperactivity disorder (ADHD) and for the quantitative evaluation of ADHD medication/therapy in diagnosed patients. This technique combines a 15 minute auditory-based test of attention with simultaneous EEG monitoring by a wireless, portable data acquisition device. This system acquires both behavioral response (i.e., reaction times to target stimuli, as well as errors of omission/commission) and EEG waveforms. All of the data is simultaneously processed by the algorithms to produce several representative indices. These indices are then combined to produce an overall neuro-behavioral index that represents the degree by which both "behavioral" and "EEG" attention is maintained throughout the test.

20 Claims, 4 Drawing Sheets

Table 1
Summary Results (Mean ± Standard Deviation of Indices)

| | EEG-Index | Behavioral Index | Neuro-Behavioral Index |
|---|---|---|---|
| Normal | 0.43±0.06 | 0.02±0.01 | 0.43 ±0.06 |
| ADHD(Before Med) | 0.76±0.29 | 0.40±0.36 | 0.92±0.29 |
| ADHD (After Med) | 0.46±0.05 | 0.23±0.24 | 0.55±0.13 |

Table 2
Result of *t* test (p-value)

| | EEG Index | Behavioral Index | Neuro-Behavioral Index |
|---|---|---|---|
| Normal vs ADHD (Before Med) | 0.017 | 0.023 | 0.0025 |
| Paired ADHD (Before Med) vs ADHD (After Med) | 0.034 | 0.069 | 0.030 |

U.S. PATENT DOCUMENTS

| | | | | |
|---|---|---|---|---|
| 6,740,032 | B2* | 5/2004 | Balkin et al. | 600/300 |
| 6,993,380 | B1* | 1/2006 | Modarres | 600/544 |
| 7,177,675 | B2* | 2/2007 | Suffin et al. | 600/544 |
| 7,269,456 | B2* | 9/2007 | Collura | 600/545 |
| 7,403,814 | B2* | 7/2008 | Cox et al. | 600/544 |
| 7,471,978 | B2* | 12/2008 | John et al. | 600/544 |
| 7,489,964 | B2* | 2/2009 | Suffin et al. | 600/544 |
| 7,509,163 | B1* | 3/2009 | Luo et al. | 600/544 |
| 7,593,767 | B1* | 9/2009 | Modarres | 600/544 |
| 7,668,591 | B2* | 2/2010 | Lee et al. | 600/544 |
| 7,686,769 | B2* | 3/2010 | Caplygin | 600/558 |
| 7,761,144 | B2* | 7/2010 | Cox et al. | 600/544 |
| 7,840,257 | B2* | 11/2010 | Chance | 600/473 |
| 7,860,561 | B1* | 12/2010 | Modarres | 600/544 |
| 7,865,234 | B1* | 1/2011 | Modarres | 600/544 |
| 7,983,741 | B2* | 7/2011 | Chance | 600/476 |
| 2002/0091335 | A1* | 7/2002 | John et al. | 600/544 |
| 2002/0183644 | A1* | 12/2002 | Levendowski et al. | 600/544 |
| 2003/0013981 | A1* | 1/2003 | Gevins et al. | 600/544 |
| 2003/0135128 | A1* | 7/2003 | Suffin et al. | 600/544 |
| 2004/0082862 | A1* | 4/2004 | Chance | 600/473 |
| 2004/0215082 | A1* | 10/2004 | Chance | 600/473 |

OTHER PUBLICATIONS

Clarke, A.R. Electroencephalogram differences in two subtypes of attention defecit/hyperactivity disorder. Physchophysiology 38(2): 212-21, 2001.

Goldman, L.S., et al. Diagnosis and treatment of attention deficit/ hyperactivity disorder in children and adolescents. JAMA 279(14): 1100-07, 1998.

Attention deficit hyperactivity disorder http://www.nimh.nih.gov/publicat/adhd.cfm.

Barry, R., et al. A review of electrophysiology in ADHD: Qualitative and quantitative electroencephalography. Clin Neurophysiol 114(2): 171-83, 2003.

* cited by examiner

FIG. 4

Table 1
Summary Results (Mean ± Standard Deviation of Indices)

| | EEG-Index | Behavioral Index | Neuro-Behavioral Index |
|---|---|---|---|
| Normal | 0.43±0.06 | 0.02±0.01 | 0.43 ±0.06 |
| ADHD (Before Med) | 0.76±0.29 | 0.40±0.36 | 0.92±0.29 |
| ADHD (After Med) | 0.46±0.05 | 0.23±0.24 | 0.55±0.13 |

Table 2
Result of $t$ test (p-value)

| | EEG Index | Behavioral Index | Neuro-Behavioral Index |
|---|---|---|---|
| Normal vs ADHD (Before Med) | 0.017 | 0.023 | 0.0025 |
| Paired ADHD (Before Med) vs ADHD (After Med) | 0.034 | 0.069 | 0.030 |

NEURO-BEHAVIORAL TEST METHOD FOR SCREENING AND EVALUATING THERAPY FOR ADHD AND SYSTEM

The present application is a continuation in part of U.S. patent application Ser. No. 11/021,594 filed Dec. 22, 2004, now U.S. Pat. No. 7,865,234, and also U.S. Provisional Patent Appln. Ser. No. 60/691,749, filed Jun. 17, 2005, which this application in part relies on for priority and both of which are hereby incorporated by reference.

The U.S. Government has a paid-up license in this invention and the right in limited circumstances to require the patent owner to license others on reasonable terms provided for by the terms of grant numbers 1R43 MH067464-01 awarded by the National Institutes of Health.

BACKGROUND OF THE INVENTION

1. Field of the Invention

The present invention relates to a method of analyzing a subject for Attention Deficit Hyperactivity Disorder (ADHD), more particularly to a quick (short duration), quantitative method of ADHD analysis, and to a system and device for performing the analysis. The present invention additionally relates to a method, which can be used to quantitatively measure the treatment endpoints for the subject, i.e., appropriate levels of stimulants.

2. Technical Background

Attention Deficit Hyperactivity Disorder (ADHD) is a disorder that inhibits an individual's capacity to regulate activity level, inhibit behavior, and attend to tasks. ADHD is the most common developmental disorder of childhood, affecting 5-15% of school age children, or approximately 2 million children in the United States. ADHD may interfere with the ability to learn or to develop satisfactory interpersonal relationships and may result in academic failure, inability to fulfill intellectual potential, poor self-esteem, or socially maladaptive behavior. In general, when ADHD is left untreated there is a gradual accumulation of adverse processes and events that increase the risk of serious psychopathology later in life.

The current ADHD diagnosis in children is subjective and varies according to the method and opinions of the specialist. Generally it involves interviewing the children, parents, teachers, and school staff, etc. The specialist will then incorporate and analyze all of the data obtained and make a decision based on his/her findings.

To overcome the problems associated with the current subjective assessment methods, a variety of objective methods of assessing the symptoms of ADHD have been devised. These tests tend to assess the level of attention, the level of activity, and the impulsivity control in an objective manner. One of the more common objective methods for studying sustained attention is the test of variation of attention (TOVA) during which the subject is asked to select stimulating signals out of a series of sequential auditory or visual signals. ADHD subjects miss stimuli more frequently (omission errors) or more often have commission errors, defined as erroneous responses to insignificant stimuli. Also, the reaction time of ADHD patients is prolonged.

Using a neurological assessment approach, a number of studies have focused on differentiating ADHD from normal subjects based on brainwave measures such as the EEG power spectrum. Since ADHD is considered a result of a CNS dysfunction, and the EEG directly measures the brain activity, it has the potential to be an appropriate tool for assessing ADHD. In particular, a recent paper by Robert Barry and their colleagues contain a comprehensive review of the previous work along with their recent findings with regards to the promising potential of EEG for detection of ADHD. These studies generally show that children with ADHD produce excess brainwaves in the lower frequency bands (e.g, theta frequency, 4-8 Hz) compared to the higher frequency bands such as alpha (8-12 Hz) and beta (15-35 Hz). For example, Ucles and Lorente's study analyzed EEG during eyes-closed resting condition (similar to the test protocol of this study) and reported that theta/alpha ratio from occipital leads can discriminate ADHD from normal children.

An object of the present invention is to introduce an objective, practical, and quantitative means of assessing ADHD by combining a portable multi-channel wireless EEG acquisition and analysis device with a quick (15-minute) auditory-based test of maintenance of attention. The system is developed for the identification and quantitative evaluation of children with ADHD and for gauging the effectiveness of medication on neurobehavioral indices and parameters.

SUMMARY OF INVENTION

The present invention relates to a method of analyzing a subject for Attention Deficit Hyperactivity Disorder (ADHD), more particularly to a quick (short duration), quantitative method of ADHD analysis, and to a system and device for performing the analysis. The present invention additionally relates to a method, which can be used to quantitatively measure the treatment endpoints for the subject, i.e., appropriate levels of stimulants.

In one embodiment, the present invention includes a method of screening for attention deficit hyperactivity disorder (ADHD) comprising the steps of measuring and analyzing EEG signals from a subject; measuring and analyzing a response of the subject to a stimulus; and determining whether the subject has attention ADHD based in part on the analyzed EEG signals and in part on the analyzed response of the subject to a stimulus.

In another embodiment, the present invention includes a method of analyzing a subject for attention deficit hyperactivity disorder (ADHD) comprising the steps of placing electrodes onto a subject's head having a brain wave signal; providing a stimulus to the subject; measuring the subject's response to the stimulus and the brain wave signal; analyzing the brain wave signal; and making a determination that the subject has ADHD based in part on the brain wave signal analysis over a period of time, and in part on the subject's response to the stimulus over the period of time.

In still another embodiment, the present invention includes a method of therapeutically treating a subject for attention deficit hyperactivity disorder (ADHD) comprising the steps of quantitatively analyzing a subjects brain wave signals and using the quantitative analysis in estimating or determining whether the subject has ADHD; making a physical change to the subject or giving the subject a medication to make an improvement to the subject's ADHD based in part on the quantitative analysis; quantitatively analyzing a second time the subjects brain wave signals to estimate or determine the extent of the improvement to the subject's ADHD; and if necessary, making an additional physical change to the subject or reducing or increasing the medication in response to the previous step.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention; and together with the description serve to explain the principles and operation of the invention.

BRIEF DESCRIPTION OF THE DRAWINGS

FIG. 4 Tables showing quantitative results of normal subject and pre- and post-medication ADHD subject.

DESCRIPTION OF THE PREFERRED EMBODIMENT

Test Hardware and Protocol

The neuro-behavioral test of ADHD is based on a modified "Odd-ball Paradigm", which refers to a test during which the subject has to distinguish frequent auditory/visual cues from infrequent ones via some form of behavioral response. While administering the test, the system acquires EEG by utilizing a lightweight (3.4 Oz with 2 AAA batteries) and compact (4.0"×2.2"×0.7") wireless EEG data acquisition unit (Cleveland Medical Devices Inc. FDA-cleared Crystal™ 16 monitor). This hardware is capable of collecting up to 8 channels of EEG and transmitting the data via a 902 to 928 MHz telemetry link to a commercial PC. One input channel of the unit has been modified to accept signals from a hand-held push-button to record the subject's cognitive response. Sitting comfortably with his/her eyes closed in a dark and quiet room, the subject is instructed to relax but maintain attention for the duration of the test. The PC, located about 6 feet away, presents a series of target and non-target auditory stimuli (less than 5 seconds apart presented in a random fashion) for a total test duration of 15 minutes. Upon hearing the target stimuli, the subject is to press a push-button while ignoring any non-target sounds. The PC then collects and displays the EEG and push-button data (subject's reaction profile).

Data Analysis

Two stages of data processing are performed as follows:

Stage I—Processing of Raw EEG and Push-Button Position Following Each Stimulus:

In the first stage, reaction time to each auditory stimulus (target/non-target) is computed based on the time delay between the presentation of the sound and pressing of the push-button (reaction time). By convention, erroneous response to a non-target stimulus (commission error) is represented by $(-1)^*$ reaction time. Also, failure to respond to a target stimulus is marked as an error of omission and is assigned a maximum value corresponding to the average inter-stimulus period.

Figure 1:
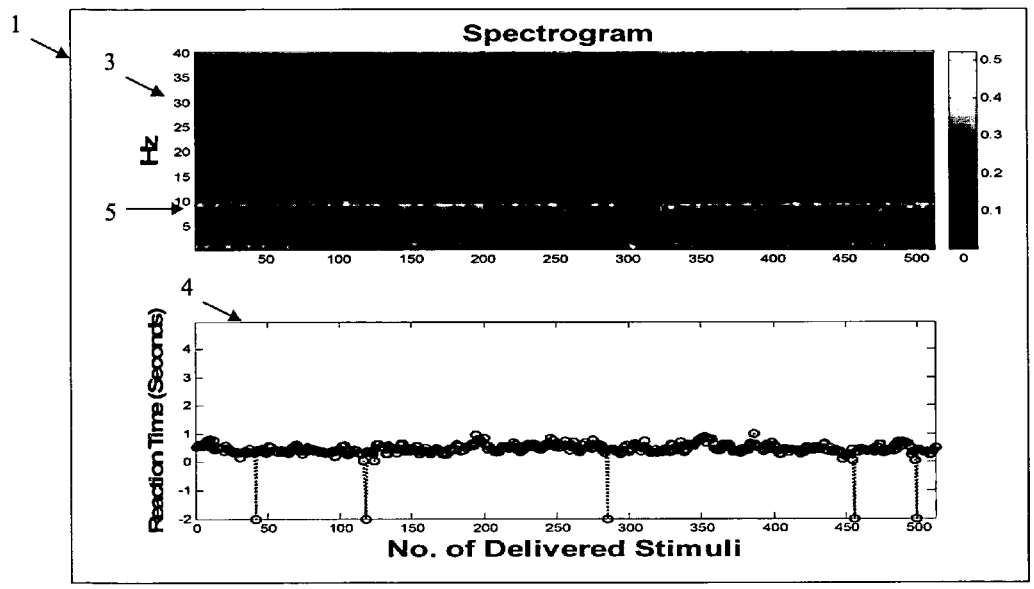
FIG. 1 Graphs showing clinical results of EEG and response of both normal subject and ADHD subject prior to taking medication FIG. 2 Graphs showing EEG and Behavioral Indexs of normal and ADHD subjects.
Figure 1:
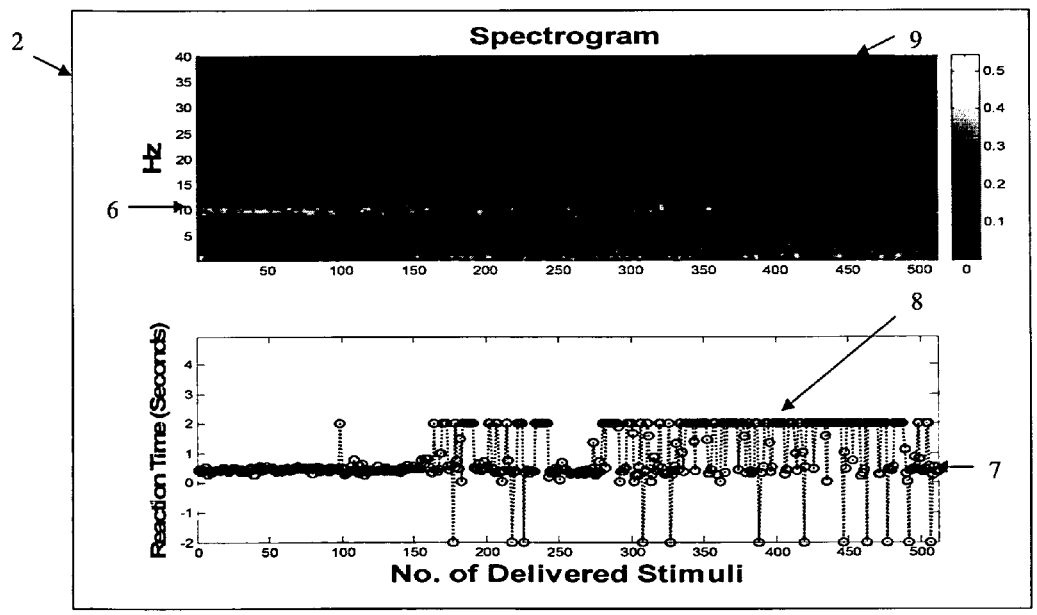

As for EEG analysis, the time-varying spectrogram (Short-Term Fourier Transform, STFT) is computed using an analysis window that spans the time period between two consecutive stimuli. Each instantaneous spectrum is further reduced to a single quantity that represents a particular characteristic of the power distribution. Examples include the relative powers in the various frequency bands as well as the ratios of such regional powers. In particular, the ratio of the integral of powers in the theta and alpha bands following each stimulus is defined and computed as follows:

$$\text{Theta/Alpha } (n) = \sum_{f \in \theta} P_n xx(f) \bigg/ \sum_{f \in \alpha} P_n xx(f) \tag{1}$$

where $P_n xx$ (f) is the power spectral density (STFT) between sample times n and n+1. Theta/Alpha is thus the instantaneous ratio of the integral of power in the $\theta$ (4-7.5 Hz) and a (8-12 Hz) frequency bands. To illustrate the above analyses, FIG. 1 shows the stage I data processing from a normal adolescent (left column) and an aged-matched teenager diagnosed with ADHD (pre-medication). For each subject, the presented results consist of the 3-dimensional spectrogram (top plot) and the reaction time profile (bottom plot). Spectrogram plots are such that for any given frequency band (horizontal slice), brighter color indicates relative higher power levels of the EEG.

Comparing the results from the two subjects, it is apparent that the ADHD diagnosed subject had many more prolonged responses as well as numerous omission and commission errors. The spectrogram of the ADHD subject also shows differences from the normal subject. Thus, it appears that unlike the normal subject, the ADHD subject's EEG power distribution profile is not maintained throughout the test duration and becomes highly variable, particularly in the alpha and sub-alpha regions, after 100 stimuli (~200 seconds in the test).

Stage II—Computation of Neurobehavioral Indices:

In the second stage of analysis, the sequence of reaction times and Theta/Alpha ratios are further processed and reduced to a few representative indices that can be used to classify ADHD from normal condition and also evaluate the effect of medication. Two dimensionless EEG-based and behavioral-based indices are thus defined and computed as follows:

$$EEG\_Index = \text{Coefficient of Variation of Theta/Alpha} \\ (n|n\epsilon N) \tag{2}$$

which is computed from the standard deviation of Theta/Alpha normalized by its mean level over an interval N, and $$Behavioral\_index = \\ (1/N) \sum_{n \in N} [\text{Prolonged-Resp } (n), \text{Commission Errors } (n)] \tag{3}$$

representing the proportion of prolonged responses (>0.6 sec, including omissions) and commission errors for the analysis interval N. The indices are defined such that their values increase as a result of inattentiveness and hyperactivity associated with ADHD.

We have also defined a neurobehavioral index that incorporates both an EEG_Index and Behavioral_Index. The exact formulation of this index was determined following the stage I and II analysis of the clinical data (described below) and will be presented in the next section under Results.

Experimental Methods and Clinical Studies

Two sets of clinical experiments were performed to examine the test's capability to discriminate normal from ADHD condition (before medication) and to track the effect of ADHD medication. These tests were approved by the CleveMed's Institutional Review Board and informed consents were obtained from all of the subjects and their parents or legal guardians.

The first set of clinical studies was performed in a patient examination room at a pediatric clinic (Dr. Senders and Associates) on five children who were diagnosed with ADHD and were currently on medication (age range: 10-15). Each session consisted of two 15-minute tests (before and after taking medication) that were administered ~1 hour apart. The first test was administered early in the morning ~15-30 minutes before their regular time of taking medication, which is when the effect of medication is at its lowest level (due to the normal washout period). Immediately following the 15-min test, patients took their normal, daily dosage and waited for one hour before repeating the 15 minute test.

The second set of tests were performed on 5 normal adolescents (age range: 10-17) who had no history of ADHD or any other mental disorders as well as no known sleep/sleepiness or respiratory problems. To minimize the compounding effects of drowsiness/mild sleepiness, resulting in diminished capability to maintain attention/alertness, subjects were instructed to get adequate sleep for three consecutive nights prior to their test. The tests were performed between 9:00 am and 11:30 am at the Sleep Laboratory of CleveMed NeuroWave Inc.

For all of these clinical tests, EEG data, sampled at 200 Hz, was obtained from the right and left hemisphere of the Frontal, Central, and Occipital regions using standard gold cup electrodes. Simultaneously recorded EEG and behavioral response data were pooled together for the statistical analysis described below.

FIG. 1 has already shown the Stage I results from a normal subject and an ADHD patient prior to taking his medication. The data of FIG. 1 was typical in that the normal adolescents demonstrated very few prolonged responses as well as errors of omission and commission. In contrast, in ADHD subjects before medication, reaction times showed numerous prolonged responses and errors starting relatively early into the test (i.e., during the first 5 minutes). The EEG spectrogram also showed apparent differences. For example, unlike the normal group, ADHD subjects' EEG contained a highly variable pattern of power distribution particularly in terms of maintaining concentrated alpha power throughout the test.

Figure 2:
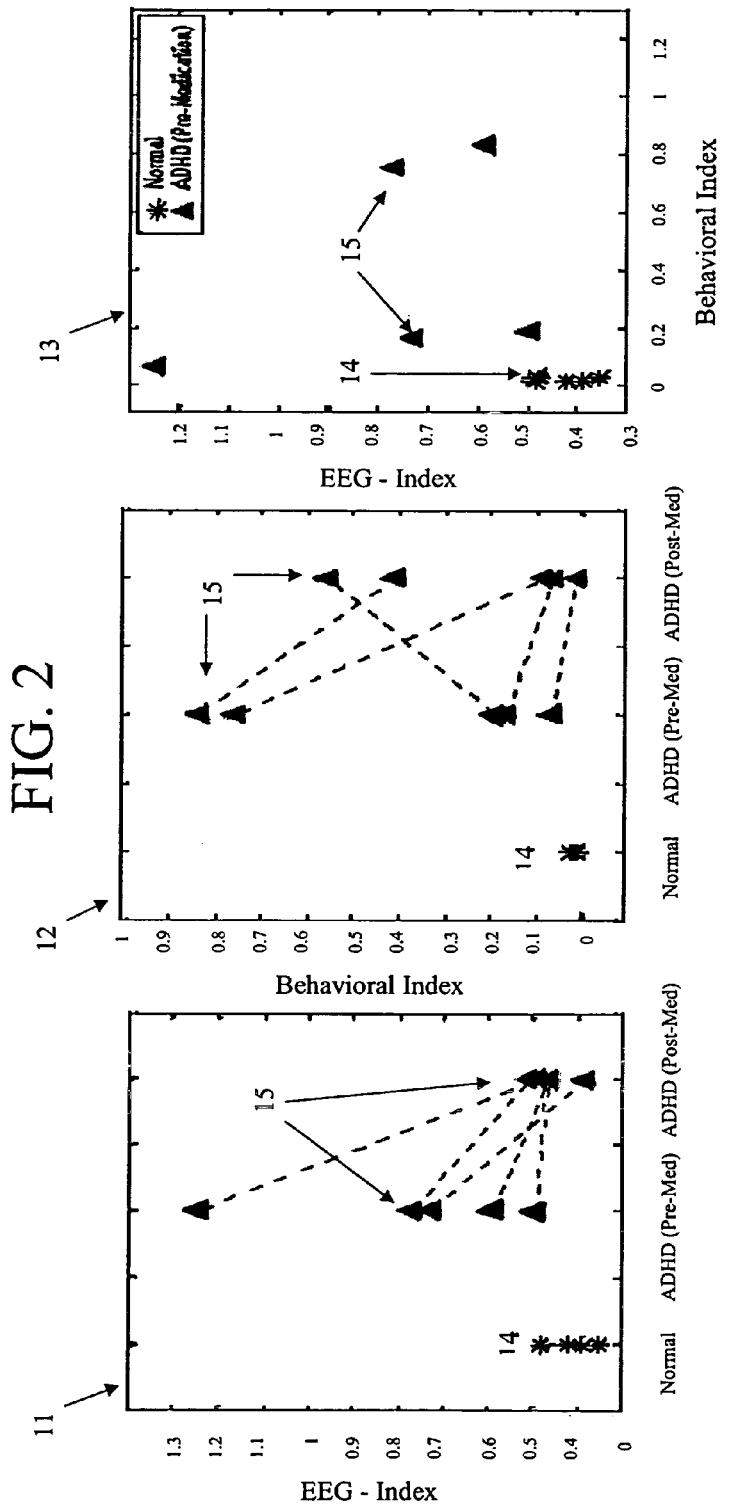

The left 11 and middle 12 plots of FIG. 2 show the individual EEG_index (occipital site) and Behavioral_index, respectively, for each of the 5 normal and 5 ADHD patients immediately before and one hour after taking their medication. These indices were computed from the first 5 minutes of the test (i.e., used N corresponding to minutes 0 to 5 in Eqs. 2 and 3). FIG. 2 clearly shows that both indices separate the normal from the ADHD (before medication) group. Furthermore, the EEG-Index of all 5 ADHD patients shows improvement after medication and drop to the same range as normal subjects. The improvement in the Behavioral-Index after medication is present in 4 of the patients, although the average values after medication seem to stay above the range of values for the normal test subjects.

The clustering of the groups in the two-dimensional space (EEG and Behavioral) was examined by plotting the EEG-Index against its corresponding Behavioral-Index from all of the normal and ADHD patients (before medication) in the right plot 13 of FIG. 2. This plot shows a clear separation of the two groups particularly if the separation boundary is defined as a diagonal line that crosses both the vertical and horizontal axes at low levels of EEG and Behavioral values. This result motivated us to define a combined index as follows:

$$\text{Neuro-Behavioral Index} = \sqrt{[EEG\_Index]^2 + [Behavioral\_Index]^2} \quad (4)$$

Figure 3:
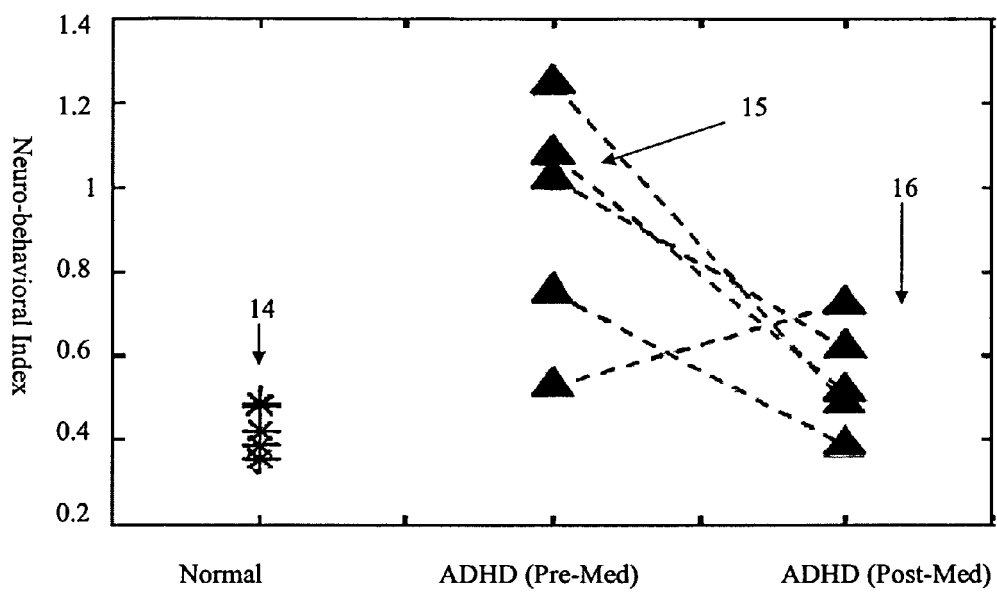
FIG. 3 Graph showing Neuro-Behavioral Index of normal subject and pre- and post-medication ADHD subject.

The Neuro-Behavioral Index of (4) is essentially the distance from the origin in the left plot of FIG. 2 and is shown in FIG. 3 for all subjects. As shown in the statistical analysis below, this combined index was more sensitive than the other previous two indices for separating various groups of subjects.

Statistical Analysis

Table 1 shows the mean and standard deviation of the three indices for all of the subject groups and is essentially a summary of the data in FIGS. 2-3. Table 2 provides the significant level (p-value) of unpaired t test comparison of the mean indices from the normal and ADHD (before medication) group. It also provides the paired t test result (p value) of data before and after medication. Table 2 results shows that the mean values of EEG-Index and Behavioral-Index are statistically smaller in normal subjects compared with the ADHD before medication group. Furthermore, it is apparent in Table 2 that combining these indices into a Neuro-Behavioral index produces an even stronger separation between the two groups as indicated by its p-value that is an order of magnitude smaller than those of the other two indices. The Neuro-behavioral Index also produced the smallest p-value for the paired comparison of data before and after ADHD medication.

The present invention includes a new method for screening/evaluating ADHD that is based on the simultaneous acquisition/analysis of EEG and a quick (15-minute) auditory-based test of maintenance of attention. The results show that a combined neurobehavioral index computed within the first 5 minutes of test data can discriminate ADHD (pre-medication) from normal condition in adolescent subjects. The test also appears to be able to track the effect of ADHD medication on neurobehavioral parameters. Further assessment of the technique is currently underway with a larger subject population that includes adult ADHD patients.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. A method of screening for attention deficit hyperactivity disorder (ADHD) comprising the steps of:
    a) measuring and, with a computer processor, analyzing EEG signals from a subject over a measurement time period;
    b) measuring and, with a computer processor, analyzing a non-EEG response of the subject to a stimulus over the measurement time period; and
    c) determining whether the subject has ADHD based in part on the analyzed EEG signals and in part on the analyzed non-EEG response of the subject to a stimulus.

2. The method in claim 1, wherein the measurement period is less than 2 hours.

3. The method in claim 2, wherein the measurement period is less than 60 minutes.

4. The method in claim 1, wherein the step of determining whether the subject has ADHD is performed by determining the distance between a first point given by an index computed from the analyzed EEG signals versus an index computed from the analyzed non-EEG response of the subject to a stimulus and a second point.

5. The method in claim 1, wherein the stimulus is supplied and the non-EEG response is measured and analyzed according to a modified odd-ball paradigm.

6. The method in claim 1, wherein the stimulus is a video device.

7. A method of therapeutically treating a subject for attention deficit hyperactivity disorder (ADHD) comprising the steps of:
 a) quantitatively analyzing, with a computer processor, a subject's brain wave signals and using the quantitative analysis in estimating or determining whether the subject has ADHD;
 b) making a physical change to the subject or giving the subject a medication to make an improvement to the subject's ADHD based in part on the quantitative analysis;
 c) quantitatively analyzing a second time the subject's brain wave signals to estimate or determine the extent of the improvement to the subject's ADHD; and
 d) if necessary, making an additional physical change to the subject or reducing or increasing the medication in response to the previous step.

8. The method in claim 7, further including a step of providing one or more types of stimulus to the subject.

9. The method in claim 8, wherein the subject is instructed to respond after recognizing one or more of the types of stimulus.

10. The method in claim 9, further including the step of measuring the subject's response to one or more types of stimulus and wherein the stimulus is provided on an intermittent basis.

11. The method in claim 7, wherein the subject is given medication and the amount of medication is increased based on the results of quantitatively analyzing the subject a second time.

12. The method in claim 7, wherein the subject is given medication and the amount of medication is decreased based on the results of quantitatively analyzing the subject a second time.

13. The method in claim 9, wherein the subject is given medication and the amount of medication is increased based on the results of quantitatively analyzing the subject a second time.

14. The method in claim 9, wherein the subject is given medication and the amount of medication is decreased based on the results of quantitatively analyzing the subject a second time.

15. A method of analyzing a subject for attention deficit hyperactivity disorder (ADHD) comprising the steps of:
 a) placing electrodes onto a subject's head having a brain wave signal;
 b) providing a stimulus to the subject;
 c) measuring the subject's non-brain-wave response to the stimulus and the brain wave signal;
 d) analyzing the brain wave signal with a computer processor; and
 e) making a determination that the subject has ADHD based in part on the brain wave signal analysis over a period of time, and in part on the subject's non-brain-wave response to the stimulus over the period of time.

16. The method in claim 15, wherein the stimulus is one or more auditory stimulus.

17. The method in claim 16, wherein the measured brain wave signal is filtered before analyzing.

18. The method in claim 17, wherein the stimulus is provided on an intermittent basis.

19. The method in claim 18, wherein a power spectrum profile is estimated or determined for each time segment of the analyzed brain wave signal, the power spectrum profile comprising an alpha component and one or more sub-alpha components and a ratio is calculated of the one or more sub-alpha components to the alpha component.

20. The method in claim 19, wherein the determination that the subject has ADHD is based in part on an average of the ratio of the one or more sub-alpha components to the alpha component either exceeding a predetermined threshold number over a period of time or a profile of the ratio over a period of time.

* * * * *